(12) United States Patent
Kim et al.

(10) Patent No.: US 10,188,441 B2
(45) Date of Patent: Jan. 29, 2019

(54) DRUG DELIVERY IMPLANT IMPLANTED INTO BONE

(71) Applicant: UNIVERSITY-INDUSTRY COOPERATION GROUP OF KYUNG HEE UNIVERSITY, Yongin-si, Gyeonggi-do (KR)

(72) Inventors: Seong-Hun Kim, Seoul (KR); Jung Sun Heo, Seoul (KR); Eun-Cheol Kim, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 232 days.

(21) Appl. No.: 15/168,110

(22) Filed: May 30, 2016

(65) Prior Publication Data

US 2017/0027628 A1 Feb. 2, 2017

(30) Foreign Application Priority Data

Jul. 28, 2015 (KR) .................. 10-2015-0106630

(51) Int. Cl.
*A61B 17/56* (2006.01)
*A61F 2/28* (2006.01)
*A61B 17/86* (2006.01)

(52) U.S. Cl.
CPC ........ *A61B 17/864* (2013.01); *A61B 17/8685* (2013.01); *A61F 2/28* (2013.01); *A61B 2017/561* (2013.01); *A61F 2250/0068* (2013.01)

(58) Field of Classification Search
CPC . A61B 17/846; A61B 17/8605; A61B 17/861; A61B 17/8615; A61B 17/862; A61B 17/8635; A61B 17/864; A61B 17/8685; A61B 17/865; A61B 17/7098; A61B 2017/561; A61M 2025/105
See application file for complete search history.

(56) References Cited

U.S. PATENT DOCUMENTS

| | | | | |
|---|---|---|---|---|
| 5,769,852 | A * | 6/1998 | Br.ang.nemark | A61B 17/8605 606/314 |
| 2007/0233123 | A1* | 10/2007 | Ahmad | A61B 17/863 606/307 |
| 2011/0046557 | A1* | 2/2011 | Lee | A61M 37/0015 604/173 |
| 2015/0011951 | A1* | 1/2015 | Hwang, II | A61C 8/0006 604/286 |

* cited by examiner

*Primary Examiner* — Nathan R Price
*Assistant Examiner* — Courtney B Fredrickson
(74) *Attorney, Agent, or Firm* — Park, Kim & Suh, LLC

(57) ABSTRACT

Disclosed is a drug delivery implant implanted into a bone. The drug delivery implant includes an implant fixture provided with an inlet formed at the upper end thereof and a drug supply cartridge coupled to the fixture, the drug supply cartridge includes a cap to close the inlet of the fixture and a cartridge main body provided under the cap, coupled with the cap and accommodated in the fixture to release a drug, and a cartridge hole to accommodate the cartridge main body and drug channels to guide the drug released from the inside of the cartridge main body to the outside of the fixture are formed in the fixture. The drug delivery implant may continuously administer the drug into bone tissues and mount the drug cartridge together with the cap in the fixture, thus facilitating mount of the drug cartridge in the fixture and replacement of the drug cartridge.

13 Claims, 13 Drawing Sheets

DRUG DELIVERY IMPLANT IMPLANTED INTO BONE

CROSS-REFERENCE TO RELATED APPLICATIONS

This application claims priority to and the benefit of Korean Patent Application No. 10-2015-0106630 filed in the Korean Intellectual Property Office on Jul. 28, 2015, the entire contents of which are incorporated herein by reference.

BACKGROUND OF THE INVENTION

Field of the Invention

The present invention relates to an implant implanted into a bone and, more particularly, to a drug delivery implant implanted into a bone at a designated position to directly inject a drug into a corresponding region.

Description of the Related Art

In general, a Drug Delivery System (DDS) relates to technology which minimizes conventional side effects of medicine and maximizes the effects of the medicine so as to effectively deliver a necessary amount of the medicine to a target region, and such a DDS is used to eliminate discomfort caused by oral or parenteral administration of medicine.

For example, when an anti-inflammatory analgesic drug is administered orally in order to treat arthritis, if the drug acts on a joint, the drug shows remedial effect at the joint but may show side effects, such as ulcers, in other regions, in particular, the stomach or intestines, and the DDS means a method or a system which reduces such side effects and maximizes the effects of the drug.

In addition, researches into an effective treatment with reduced patient discomfort by introducing new methods into the delivery paths and delivery types of drugs in consideration of unique physicochemical properties and pharmacokinetic properties of treatments or the drugs are now underway.

However, in the case of a patient with a chronic disease requiring continuous drug administration for long periods of time, oral administration of drugs is most common but it may be difficult for the patient to regularly take the drugs for a long period of time, even if drug formations are excellent. Such a difficulty serves as a factor obstructing treatment of chronic disease and suppression of deterioration of the chronic disease, and further causes considerable loss in terms of individual health and national economy due to leftover drugs.

In order to treat diabetes, which is a representative chronic disease, an insulin pump has been developed now and obtained excellent results in which continuous drug administration and maintenance of a drug concentration are achieved, but causes pain and fear due to use of an injection syringe and movement restriction in daily life.

In addition, hypertension medicines, Parkinson's disease medicines, and contraceptive pills need to be administered regularly for long periods of time and, if a patient does not take medicines on time, his/her health may deteriorate or desired efficacy of the medicines may not be acquired.

Recently, a bionic implant implanted into a bone, which is referred to as a drug injection implant or a drug delivery implant, has been developed and drug administration may be carried out via a drug delivery implant fixed to a bone of a designated region.

SUMMARY OF THE INVENTION

Therefore, the present invention has been made in view of the above problems, and it is an object of the present invention to provide a drug delivery implant implanted into a bone of a designated region, which may easily mount a drug cartridge (drug receptor) of a small size in an implant fixture, allow the drug cartridge to be easily replaced with a new one, and directly release/administer a drug to the corresponding region.

It is another object of the present invention to provide a drug delivery implant implanted into a bone, which may minimize damage to bone tissues into which the implant is implanted and acquire stable implantation.

It is yet another object of the present invention to provide a drug delivery implant implanted into a bone, which may prevent drug release before a drug cartridge is mounted in an implant fixture and then slowly execute drug release after the drug cartridge is mounted in the implant fixture.

In accordance with the present invention, the above and other objects can be accomplished by the provision of a drug delivery implant implanted into a bone, including a hollow-type implant fixture provided with an inlet formed at the upper end thereof, and a drug supply cartridge coupled to the fixture, wherein the drug supply cartridge includes a cap for closing the inlet of the fixture and a cartridge main body provided under the cap, coupled with the cap so as to be mounted in the fixture integrally with the cap, and accommodated in the fixture to release a drug, wherein a cartridge hole to accommodate the cartridge main body and drug channels to guide the drug released from the inside of the cartridge main body to the outside of the fixture are formed in the fixture.

The cap may be detachably coupled to the upper part of the fixture. A female screw can be formed on any one of the cap and the fixture and a male screw for screw connection with the female screw can be formed on the other of the cap and the fixture.

The fixture may include an upper fixing part forming the upper end portion of the fixture, provided with a first male screw formed on the outer circumferential surface thereof for being adapted to be fixed to a bone, and coupled with the cap, a lower fixing part forming the lower end portion of the fixture and provided with a second male screw formed on the outer circumferential surface thereof for being adapted to be fixed to the bone, and a screwless drug release part having a hollow shape connecting the upper fixing part and the lower fixing part and provided with the drug channels.

The second male screw of the lower fixing part may be a tapping screw.

And the lower fixing part may include at least one drug channel to guide the drug from the inside of the cartridge hole to the outside of the lower fixing part.

The cartridge main body may include an outer membrane including first release holes to release the drug to the outside of the cartridge main body and forming an outer cover of the cartridge main body, and an inner membrane including second release holes closed by the outer membrane, stacked in the outer membrane and closing the first release holes. And the first release holes and the second release holes may be selectively communicable with each other by external force applied to the cartridge main.

The cartridge hole may include a cartridge pressing part to pressurize the cartridge main body inserted into the fixture so as to cause release of the drug from the cartridge main body.

The cartridge pressing part may be configured to pressurize the outer membrane of the cartridge main body and thus form drug release paths in the cartridge main body so that the drug is released through the first release holes and the second release holes.

The cartridge pressing part may protrude upwards from the bottom of the cartridge hole.

The fixture may include a cartridge stimulating part to stimulate the cartridge main body inserted into the fixture so as to cause release of the drug from the cartridge main body.

The cartridge stimulating part may protrude from the inner surface of the cartridge hole so as to penetrate the cartridge main body to release the drug from the cartridge main body.

A tool groove for connection with a tool to rotate the fixture may be formed at the upper end of the fixture.

And a drug inlet may be provided at the upper end of the cartridge main body and the upper end of the cartridge main body is sealed by the cap.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
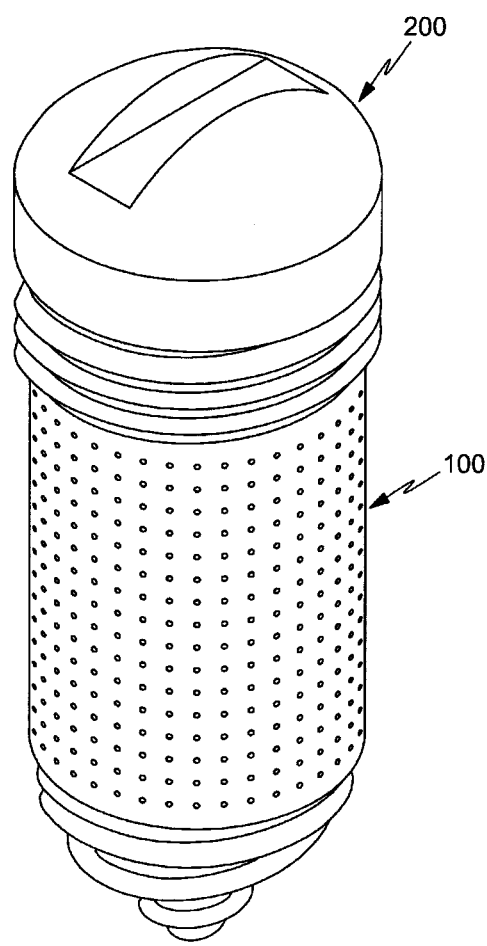
FIG. 1 is a perspective view illustrating a drug delivery implant implanted into a bone in accordance with one embodiment of the present invention.

Now, embodiments of the present invention will be described in detail with reference to the accompanying drawings. In description of the embodiments of the invention, the same or similar elements are denoted by the same reference numerals even though they are depicted in different drawings.

Figure 2:
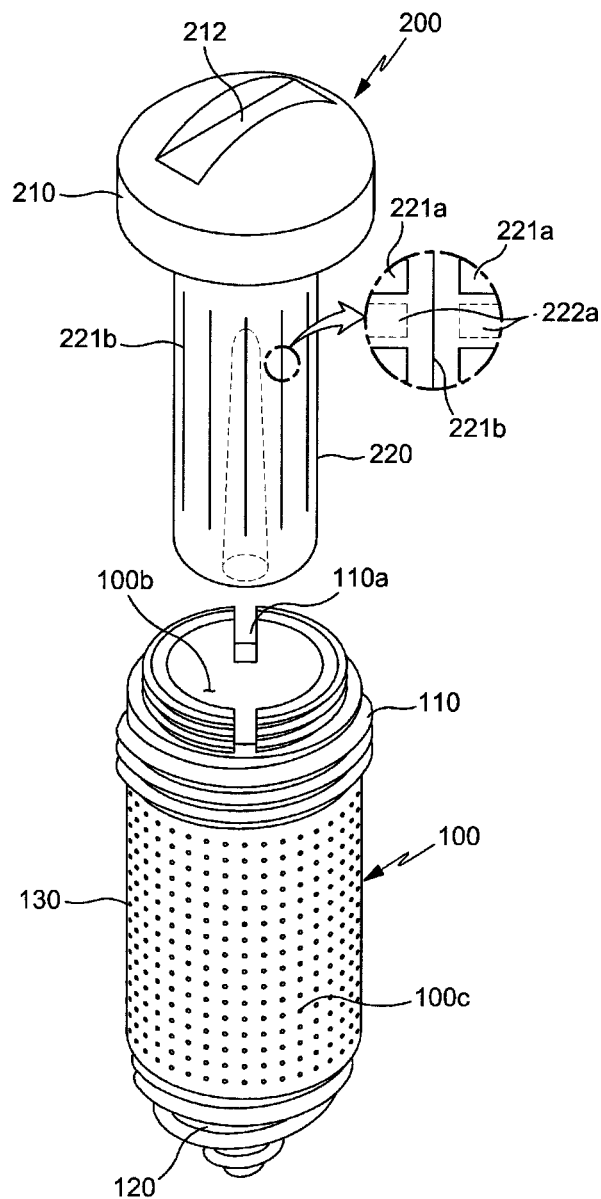
FIG. 2 is an exploded perspective view of the drug delivery implant shown in FIG. 1.
Figure 3:
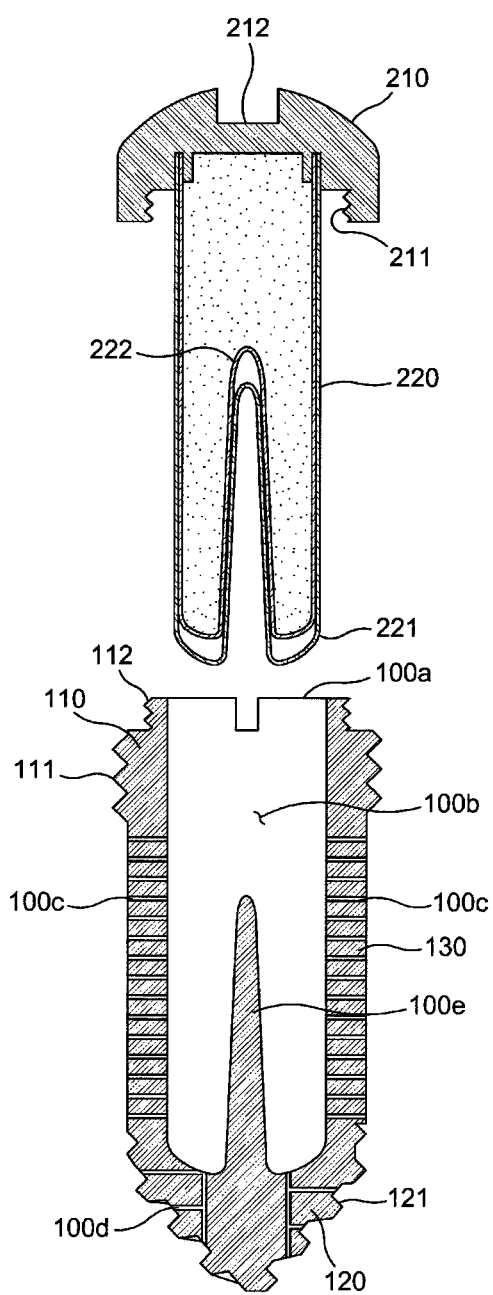
FIG. 3 is a cross-sectional view illustrating a fixture of the drug delivery implant shown in FIG. 2.
Figure 4:
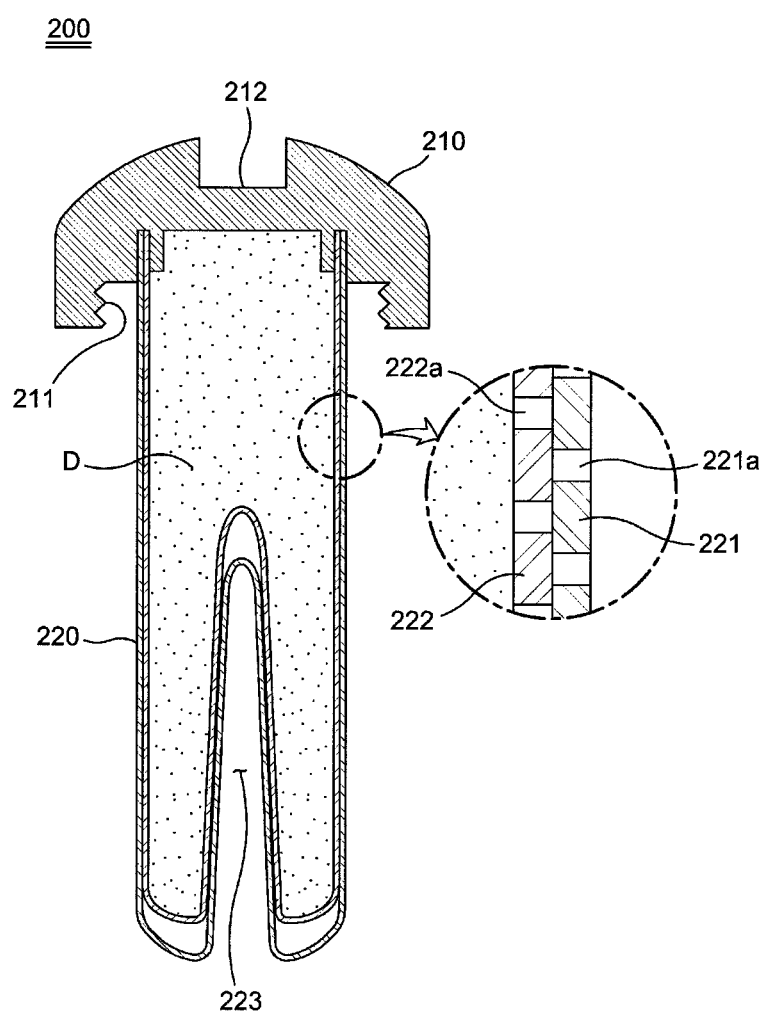
FIG. 4 is a cross-sectional view illustrating a drug cartridge of the drug delivery implant shown in FIG. 1.

First, a drug delivery implant implanted into a bone in accordance with one embodiment of the present invention will be described with reference to FIGS. 1 to 4. FIG. 1 is a perspective view illustrating a drug delivery implant implanted into a bone in accordance with one embodiment of the present invention, FIG. 2 is an exploded perspective view of the drug delivery implant shown in FIG. 1, FIG. 3 is a cross-sectional view illustrating a fixture of the drug delivery implant shown in FIG. 2, and FIG. 4 is a cross-sectional view illustrating a drug cartridge of the drug delivery implant shown in FIG. 1.

A drug delivery implant 10 implanted into a bone (hereinafter, referred to as a "drug delivery implant") in accordance with one embodiment of the present invention includes an implant fixture 100 and a drug supply cartridge 200 installed to the fixture 100.

The fixture 100 is configured so as to be implanted into bone tissues and then fixed to the bone tissues. The fixture 100 forms a base part of the drug delivery implant 10 and supports and accommodates the drug supply cartridge 200, and the drug supply cartridge 200 (hereinafter, referred to as a "drug cartridge") serves as a drug storage unit to contain a drug satisfying therapeutic purposes.

The fixture 100 has a hollow shape, i.e., a shape, the interior of which is vacant, and an inlet 100a to mount the drug cartridge 200 in the fixture 100 is formed at the upper end of the fixture 100. That is, the entirety or a part of the upper end of the fixture 100 is opened.

In the present invention, a part of the fixture 100 provided with the inlet 100a, i.e., a drug cartridge insertion hole, will be defined as the upper end of the fixture 100 regardless of the implantation direction of the fixture 100.

The drug cartridge 200 is coupled to the fixture 100 and releases the drug to the inside of the fixture 100. The drug cartridge 200 includes a cap 210 and a cartridge main body 220. The cap 210 is coupled with the upper end of the fixture 100 and serves to close the inlet 100a of the fixture 100, thereby sealing the fixture 100.

Further, the cartridge main body 220 is provided under the cap 210 so as to be coupled with the cap 210. In more detail, the cartridge main body 220 together with the cap 210 is mounted in the fixture 100 under the condition that the cartridge main body 220 is provided integrally with the cap 210, i.e., fixed to the cap 210. If the cartridge main body 220 is not formed of a biodegradable material, when the cap 210 is separated from the fixture 100, the cartridge main body 220 together with the cap 210 may be separated from the fixture 100 and replaced with a new one.

The cartridge main body 220 is accommodated in the fixture 100 and releases the drug D. Further, a cartridge hole 100b to accommodate the cartridge main body 220 and drug channels 100c to guide the drug, released from the cartridge main body 220, to the outside of the fixture 100 from the inside of the cartridge hole 100b are formed in the fixture 100.

In this embodiment, the cartridge hole 100b is depressed downwards from the upper end of the fixture 100 in the axial direction, and the inlet 100a of the fixture 100 becomes an inlet of the cartridge hole 100b.

Further, the cap 210 may be detachably coupled to the upper part of the fixture 100. In this embodiment, the cap 210 and the fixture 100 are coupled together by a screw connection method. For this purpose, a female screw may be formed on any one of the cap 210 and the fixture 100 and a male screw for screw connection with the female screw may be formed on the other of the cap 210 and the fixture 100.

With reference to FIGS. 2 and 3, the fixture 100 in accordance with this embodiment includes an upper fixing part 110, a lower fixing part 120, and a drug release part 130.

The upper fixing part 110 forms the upper end portion of the fixture 100 and is coupled with the cap 210. A first male screw 111 for fixing the fixture to a bone is formed on the outer circumferential surface of the upper fixing part 110, and the first male screw 111 firmly fixes the upper part of the fixture 100 to bone tissues.

In this embodiment, a male screw for coupling with the cap 210 is formed on the outer circumferential surface of the fixture 100, and a female screw for coupling with the fixture 100 is formed on the cap 210.

A male screw 112 for screw connection with the cap 210 (i.e., the cap fastening screw) is formed above the first male screw 111, more particularly, on the outer circumferential surface of the upper end of the fixture 100. The upper fixing part 110 has a stepwise shape so that the outer diameter of a part of the upper fixing part 100 provided with the first male screw 111 is greater than the outer diameter of a part of the upper fixing part 100 provided with the cap fastening screw 112 but the exterior of the upper fixing part 110 is not limited thereto, and the upper surface of the upper fixing part 110 is opened and thus forms the above-described inlet 100*a* of the fixture 100.

Further, a tool groove 110*a* for connection with a fixture implantation tool to rotate the fixture 100 is formed at the upper end of the fixture 100. In more detail, the tool groove 110*a* is formed on the upper fixing part 110 so that the tip of a tool (a driver) may be inserted into the tool groove 110*a*.

Further, the lower fixing part 120 forms the lower end portion of the fixture 100. A second male screw 121 for anchoring at the bone is formed on the outer circumferential surface of the lower fixing part 120, and the second male screw 121 is stuck into bone tissues and thus firmly fixes the lower end part of the fixture 100 to the bone tissues.

Thereafter, the drug release part 130 is a screwless part, the outer circumferential surface of which is provided with no screw thread. The drug release part 130 has a hollow shape connecting the upper fixing part 110 and the lower fixing part 120 to each other, and the above-described drug channels 100*c* are formed on the drug release part 130.

In this embodiment, the drug release part 130 has a cylindrical shape having a smooth surface. The drug channels 100*c* pass through a circumferential wall of the drug release part 130 so as to communicate the inside and the outside of the drug release part 130 with each other, and guides a drug to the outside of the drug release part 130 from the inner space of the drug release part 130 (i.e., the cartridge hole 100*b*).

Of course, the drug may be released through the drug release part 130 and be additionally released through other parts. For example, at least one drug channel 100*d* (hereinafter, referred to as a "lower drug channel") may be formed at the lower fixing part 120 so that the drug may be released through the lower fixing part 120.

In this embodiment, the second male screw 121 formed on the lower fixing part 120 is a tapping screw having a structure which may dig into bone tissues when the fixture 100 is rotated, and the maximum outer diameter of the second male screw 121 formed on the lower fixing part 120 is equal to or smaller than the outer diameter of the drug release part 130 and the root diameter of the first male screw 111 formed on the upper fixing part 110 is equal to the outer diameter of the drug release part 130 without being limited thereto.

The fixture 100 may be formed of any material applicable to human bodies, i.e., a material having biocompatibility, without limitation, for example, one selected from the group consisting of titanium, magnesium, iron, aluminum and copper, or an alloy including two or more selected from the group.

Particularly, since titanium has excellent characteristics as a material for a bionic implant, the fixture 100 may be formed of titanium or a titanium alloy without being limited thereto.

If the fixture 100 is formed of a biodegradable metal, such as magnesium or a magnesium alloy, the fixture 100 is degradable in the body as time passes and, in this case, the drug cartridge 200 may be formed of a biodegradable material.

With reference to FIGS. 3 and 4, the cap 210 is coupled to the upper end of the cartridge main body 220 and thus moves integrally with the cartridge main body 220, a female screw 211 corresponding to the cap fastening screw 112 is formed at the rim of the cap 210, and a tool groove 212 into which the tip of a driver is inserted is formed on the upper surface of the cap 210. Of course, the cap 210 may have a polygonal shape, for example, a hexagonal shape, so as to be rotated by a wrench.

The cartridge main body 220 stores a drug, as described above, and in this embodiment, the cartridge main body 20 has a container structure, the inside of which is vacant so as to contain the drug and, more particularly, has a container structure having a plurality of membranes, for example, a capsule, the upper end of the cartridge main body 220 is fixed to the lower part of the cap 210, and the drug is accommodated in the cartridge main body 220. For example, the upper end of the cartridge main body 220 may be inserted into the lower part of the cap 210 or be fixed to the lower part of the cap 210 through various methods, such as a screw connection method.

In this embodiment, a drug inlet is formed at the upper end of the cartridge main body 220, and the upper end of the cartridge main body 220 provided with the drug inlet is sealed by the cap 210. Of course, the cartridge main body 220 may have a porous structure, such as a sponge structure, rather than a container structure, such as a capsule.

In this embodiment, the cartridge main body 220 has a double-layered membrane structure and, more particularly, includes an outer membrane 221 forming an outer cover of the cartridge main body 220 and an inner membrane 222 stacked on the inner surface of the outer membrane 221.

With reference to FIG. 4, first release holes 221*a* to release the drug to the outside are formed on the outer membrane 221, and the first release holes 221*a* are closed by the inner membrane 222 before the drug cartridge 200 is mounted in the fixture 100.

Further, second release holes 222*a* closed by the outer membrane 221 are formed on the inner membrane 222, and the second release holes 222*a* selectively communicate with the first release holes 221*a* and thus release the drug stored in the cartridge main body 220 to the outside.

In more detail, before the drug cartridge 200 is mounted in the fixture 100, the first release holes 221*a* and the second release holes 222*a* are respectively closed by the inner membrane 222 and the outer membrane 221 and thus release of the drug is prevented and, after the drug cartridge 200 is mounted in the fixture 100, the first release holes 221*a* and the second release holes 222*a* communicate with each other and thus drug release paths are formed on the membranes 221 and 222 of the cartridge main body 220.

In this embodiment, the first release holes 221*a* and the second release holes 222*a* may communicate with each other by external force applied to the cartridge main body 220 so that the drug may be released from the inside of the cartridge main body 220 to the outside of the cartridge main body 220.

The cartridge main body 220 is mounted in the fixture 100 and pressurized by the surface of the cartridge hole 100b and, thereby, the first release holes 221a and the second release holes 222a communicate with each other.

The cartridge hole 100b pressurizes the outer membrane 221 of the cartridge main body 220 and thus causes relative displacements of the outer membrane 221 and the inner membrane 222 and, as a result, the first release holes 221a and the second release holes 222a are opened.

In this embodiment, as the cartridge main body 220 is mounted in the fixture 100, the outer membrane 221 is pushed by the surface of the cartridge hole 100b and thus pressurized in the upward direction. In more detail, the cartridge hole 100b may include a cartridge pressing part 100e which pressurizes the cartridge main body 220 inserted into the fixture 100 and thus causes release of the drug from the cartridge main body 220.

That is to say, the cartridge pressing part 100e may pressurize the outer membrane 221 of the cartridge main body 220 and thus form drug release paths on the cartridge main body 220 so that the drug may be released through the first release holes 221a and the second release holes 222a.

In this embodiment, the cartridge pressing part 100e has a structure protruding towards the inside of the cartridge hole 100b, for example, a structure protruding upwards from the bottom of the cartridge hole 100b in this embodiment, but the disclosure is not limited thereto.

Further, if a protruding structure is not applied to the cartridge hole 100b but a ratio of the depth of the cartridge hole 100b to the height of the cartridge main body 220 is adjusted so that the bottom of the cartridge main body 220 is pressurized upwards by the bottom of the cartridge hole 100b, relative displacements of the outer membrane 221 and the inner membrane 222 may occur.

In this embodiment, the outer membrane 221 of the cartridge main body 220 is pressurized upwards by the cartridge hole 100b, in particular, the cartridge pressing part 100e and thus swells outwards, and, as a result, a gap is generated between the outer membrane 221 and the inner membrane 222, the first release holes 221a and the second release holes 222a communicate with each other and the above-described drug release paths are formed in the outer and inner membranes 221 and 222 of the cartridge main body 220.

The outer and inner membranes 221 and 222 forming the cartridge main body 220 are formed of a material having excellent biocompatibility, for example, a polymeric material, such as Teflon, polypropylene or polydimethylsiloxane (PDMS), without being limited thereto. The outer and inner membranes 221 and 222 forming the cartridge main body 220 may be formed of a metal or a biodegradable material. Further, the outer membrane 221 and the inner membrane 222 may be formed of the same material or different materials.

For example, the inner membrane 222 may be a thin film formed of a metal having relatively excellent rigidity, for example, stainless steel (SST), and the outer membrane 221 may be a thin film formed of a polymeric material, such as Teflon.

Further, the drug stored in the cartridge main body 220 may include, for example, immune response changing factors, an anti-proliferative agent, an anti-mitotic agent, an anti-platelet agent, platinum coordination complexes, hormones, an anticoagulant, a fibrin decomposer, an antisecretory agent, an anti-migration agent, an immunosuppressant, an angiogenic drug, an angiotensin receptor blocker, a nitric oxide donor, antisense oligonucleotides and composites thereof, a cell cycle inhibition substance, a corticosteroid, a hemostatic steroid, an antiparasitic, glaucoma medication, an antibiotic, a differentiation regulating substance, antiviral agents, anti-cancer agents, anti-inflammatory agents, growth factors, physiologically active substances, etc. In addition, another single drug or a composite of other drugs satisfying therapeutic purposes may be stored in the cartridge main body 220, i.e., in the inner membrane 222.

For example, the growth factors may include bone morphogenetic proteins (BMPs), epidermal growth factor (EGF), erythropoietin (EPO), fibroblast growth factor (FGF), hepatocyte growth factor (HGF), insulin-like growth factor (IGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-8), vascular endothelial growth factor (VEGF), placental growth factor (PIGF), adrenomedullin (AM), autocrine mobility factor, granulocyte-colony stimulating factor (G-CSF), granulocyte-macrophage colony stimulating factor (GM-CSF), growth differentiation factor-9 (GDF-9), IL-1, IL-2, IL-3, IL-4, IL-5, IL-6, IL-7, etc.

Further, the physiologically active substances may include transforming growth factors which stimulate proliferation and differentiation of osteoblasts forming bones, insulin-like growth factor, bone morphogenetic growth materials, such as bone morphogenetic proteins, an antibiotic, etc.

The lengths of the fixture 100 and the drug cartridge 200, in particular, the cartridge main body 220, of the above-described drug delivery implant 10 may be adjusted according to conditions, such as the thicknesses of hard tissues (the bone) and soft tissues (the skin) of a region, into which the drug delivery implant 10 is implanted, and drug doses.

Further, a plurality of incision parts 221b (with reference to FIG. 2) elongated in the vertical direction may be provided on the outer membrane 221 of the cartridge main body 220. The incision parts 221b are formed at positions separated from each other in the circumferential direction of the cartridge main body 220 and are broadened when the cartridge main body 220 receives pressure in the vertical direction by the cap 210 and the cartridge hole 110b and thus the outer membrane 221 swells outwards. Therefore, the incision parts 221b correspond to a variation of the first release holes 221a.

Hereinafter, with reference to FIGS. 5A to 5C, FIGS. 6A and 6B and FIG. 7, an operating process of the drug delivery implant 10 in accordance with one embodiment of the present invention will be described in more detail.

When an implanted position of the drug delivery implant 10, i.e., a target position for drug administration, is determined, the fixture 100 is implanted into a bone B of the corresponding position. In order to implant the fixture 100, an operator opens soft tissues and forms a fixture implantation hole at a predetermined region of the bone B using a drill.

For example, the depth of the fixture implantation hole may correspond to about a length from the upper end of the first male screw 111 to a boundary between the drug release part 130 and the lower fixing part 120 (indicated by d in FIG. 5A), and the diameter of the fixture implantation hole may be substantially the same as the outer diameter of the drug release part 130.

When the fixture 100 is inserted into the fixture implantation hole and is then rotated using a driver, the lower fixing part 120 digs into the bottom of the fixture implantation hole and is thus firmly fixed to the fixture implantation hole, and the upper fixing part 110 is coupled to the inlet of the fixture implantation hole through the screw connection method and is thus fixed to the bone B.

Figure 5A:
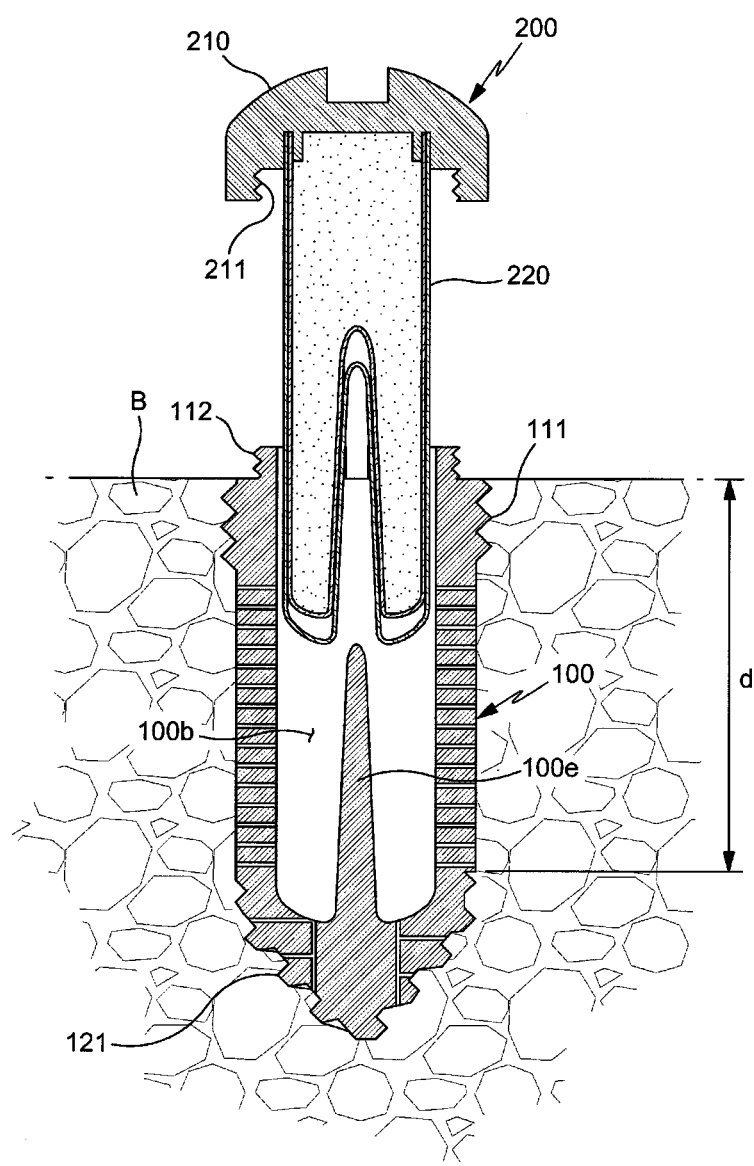
FIGS. 5A to 5C are cross-sectional views illustrating a process for mounting the drug cartridge in the fixture.
Figure 5B:
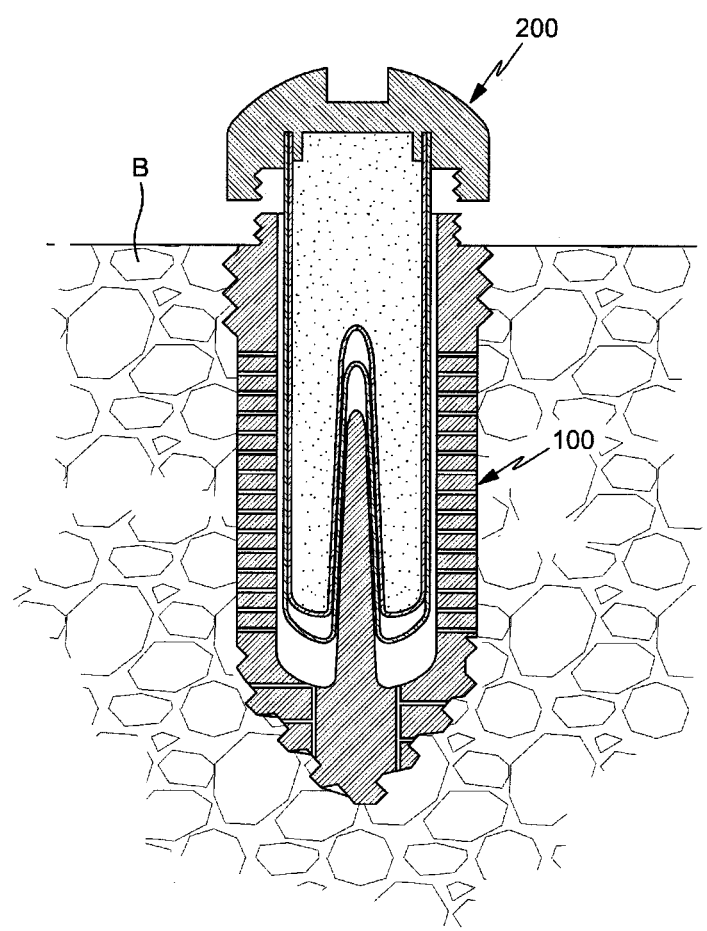
Figure 5C:
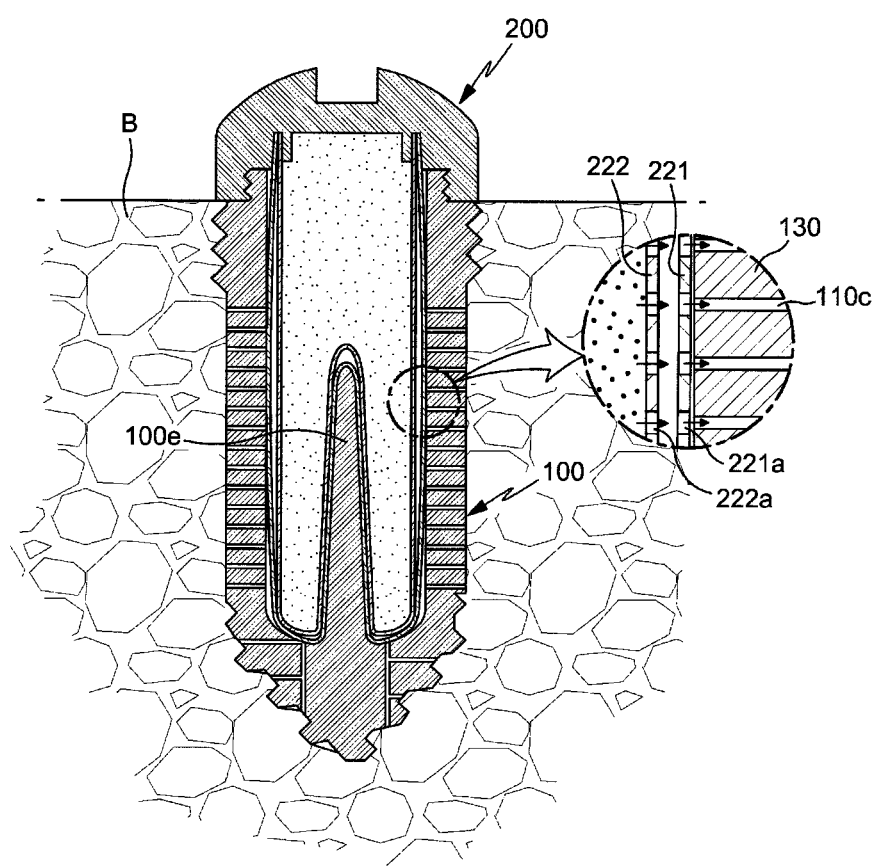

Thereafter, as exemplarily shown in FIGS. 5A and 5B, when the cartridge main body 220 is inserted into the cartridge hole 100b of the fixture 100 and then the cap 210 is fastened to the upper fixing part 110 of the fixture 100 by rotation of the cap 210, the drug cartridge 200 is fixed to the fixture 100 and the fixture 100 is sealed by the cap 210, as exemplarily shown in FIG. 5C.

Then, the outer membrane 221 of the cartridge main body 220 is pressurized upwards and the side surface of the outer membrane 221 swells outwards. Thereby, the drug release paths are opened and the drug stored in the cartridge main body 220 slowly passes throughout the bone B, i.e., bone tissues, through the drug channels 100c.

Figure 6A:
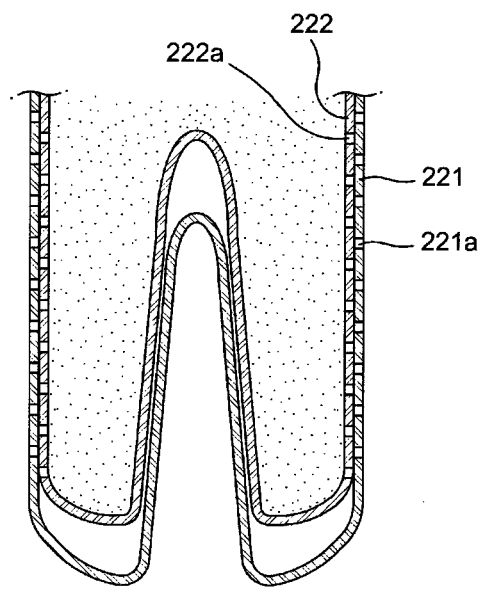
FIGS. 6A and 6B are cross-sectional views schematically illustrating the drug cartridge before and after mounting of the drug cartridge in the fixture.
Figure 6B:
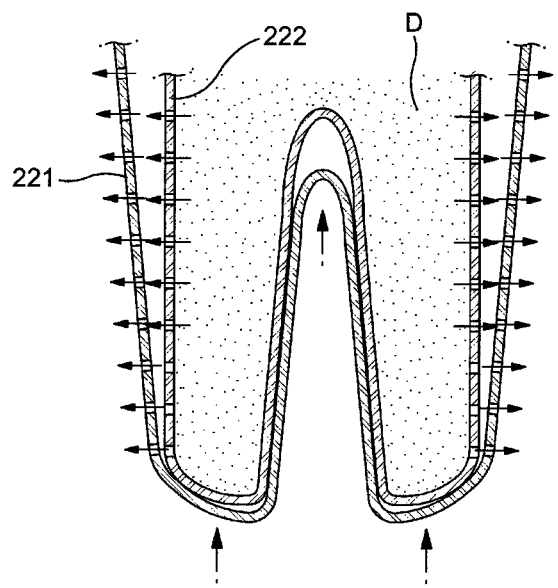

FIG. 6A illustrates a state of the drug cartridge 200 before the outer membrane 221 of the cartridge main body 220 is pressurized upwards, and FIG. 6B illustrates a state of the drug cartridge 200 in which the outer membrane 221 of the cartridge main body 220 is pressurized upwards and thus swells outwards, a gap is formed between the outer membrane 221 and the inner membrane 222 and the drug release paths are opened.

Figure 7:
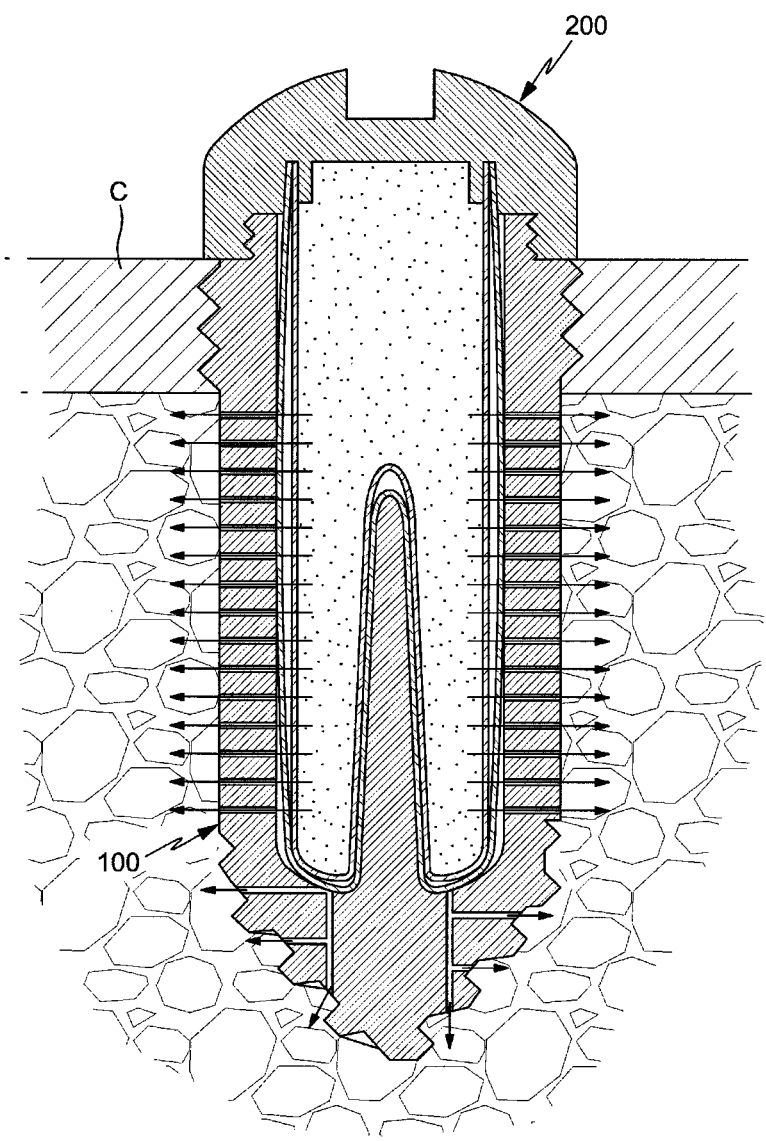
FIG. 7 is a cross-sectional view illustrating a state in which a drug delivery implant in accordance with one embodiment of the present invention is implanted into hard tissues in the oral cavity.

FIG. 7 illustrates a state of the drug delivery implant in accordance with the above-described embodiment which is implanted into a bone in the oral cavity, for example, the palatal bone or the jawbone. Here, the upper fixing part 110 is fixed to the hard cortical bone C and the drug release part 130 releases a drug, for example, a bone regeneration or growth substance, into the trabecular bone (spongy bone).

Figure 8A:
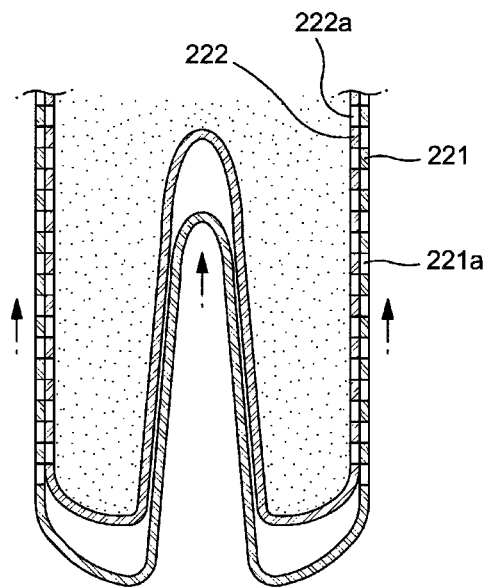
FIGS. 8A and 8B are cross-sectional views illustrating another opening mechanism of the drug cartridge.
Figure 8B:
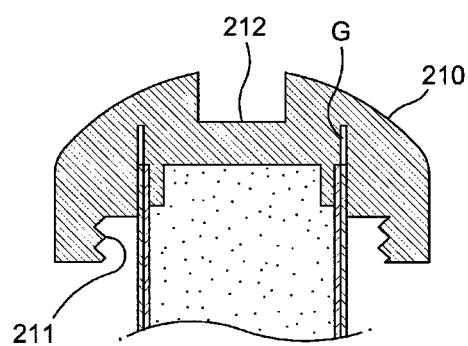

Further, in the case of a membrane structure of a cartridge main body 220 shown in FIGS. 8A and 8B, when an outer membrane 221 of a cartridge main body 220 is pressurized upwards by a cartridge hole 100b, the outer membrane 221 is pushed upwards along the surface of an inner membrane 222 and thus first release holes 221a and second release holes 222a communicate with each other, as exemplarily shown in FIG. 8A. Therefore, the structure of the cartridge main body 220 in accordance with this embodiment may omit the incision parts 221b in accordance with the former embodiment. However, a guide structure to guide rectilinear rise of the outer membrane 221 may be applied to the membrane structure of the cartridge main body 220 in accordance with this embodiment. For example, a guide protrusion may be formed in the vertical direction on the outer surface of the inner membrane 222 and a guide groove or guide hole into which the guide protrusion is inserted may be formed in the vertical direction on the outer membrane 221.

For this purpose, a gap G to allow the outer membrane 221 to be raised is formed at the cap 210, in particular, a part of the cap 210 to which the upper end of the cartridge main body 220 is connected, as exemplarily shown in FIG. 8B.

Figure 9:
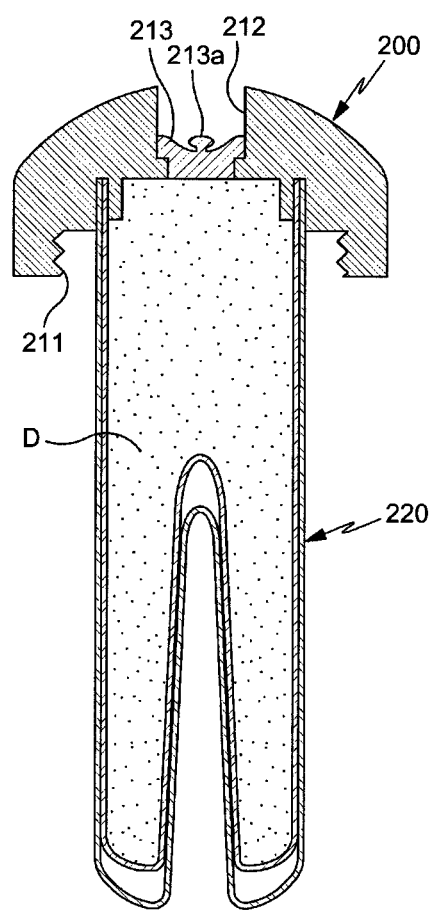
FIG. 9 is a cross-sectional view illustrating another embodiment of a drug cartridge applicable to a drug delivery implant implanted into a bone in accordance with the present invention.
Figure 10:
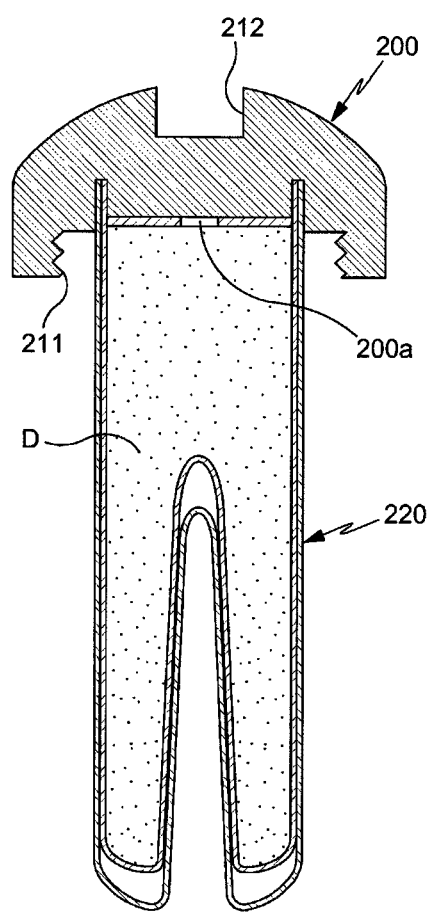
FIG. 10 is a cross-sectional view illustrating yet another embodiment of a drug cartridge applicable to a drug delivery implant implanted into a bone in accordance with the present invention.

FIGS. 9 and 10 are cross-sectional views illustrating other embodiments of drug cartridges applicable to a drug delivery implant implanted into a bone in accordance with the present invention.

With reference to FIG. 9, a drug cartridge 200 is configured such that a drug supply hole to supply a drug to the inside of a cartridge main body 220 is formed on a cap 210 and the drug supply hole is closed by a drug sealing cap 213. In order to open the drug sealing cap 213, a grip portion 213a may be formed on the drug sealing cap 213. When an operator grasps the grip portion 213a using a tool, such as tweezers, and then pulls the drug sealing cap 213 upwards, the drug supply hole is opened. The grip portion 213a is not limited to the shape shown in FIG. 9 and may have any shape as long as the drug sealing cap 213 may be opened by the grip portion 213a.

A drug cartridge 200 shown in FIG. 10 is configured such that a drug inlet 200a is formed at the upper end of a cartridge main body 220 and the upper end of the cartridge main body 220, i.e., the drug inlet 200a, is sealed by a cap 210. In the drug cartridges 220 in accordance with the above-described embodiments, the upper surfaces of the cartridge main bodies 220 are completely opened but, in the drug cartridge 220 in accordance with this embodiment, only a part, in particular, the central part, of the upper surface of the cartridge main body 220 is opened and the above-described drug sealing cap 213 and the drug supply hole may be applied to the drug cartridge 220 in this embodiment.

Figure 11:
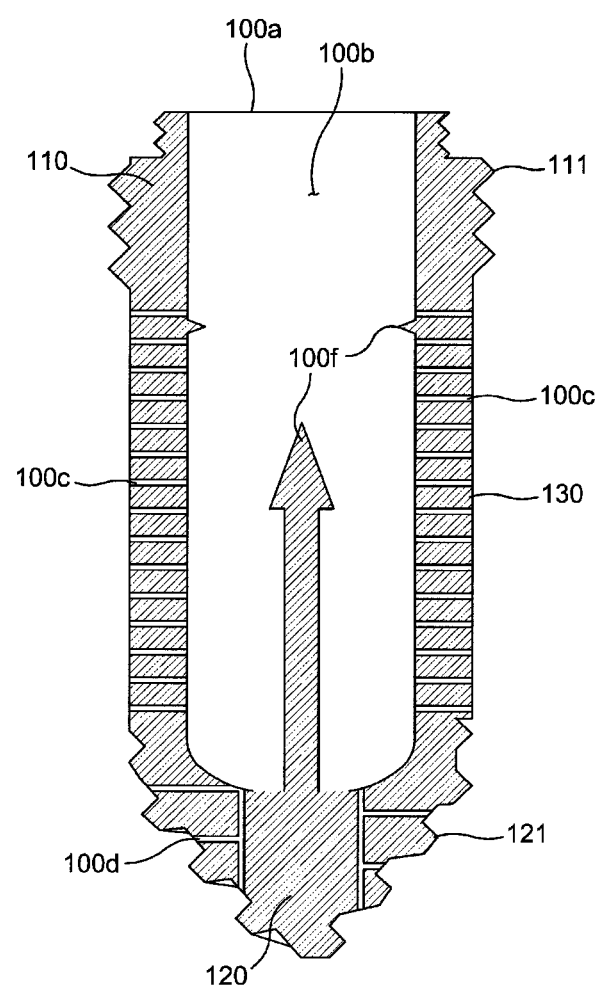
FIG. 11 is a cross-sectional view illustrating another embodiment of a fixture applicable to a drug delivery implant implanted into a bone in accordance with the present invention.

FIG. 11 is a cross-sectional view illustrating another embodiment of a fixture applicable to a drug delivery implant implanted into a bone in accordance with the present invention.

With reference to FIG. 11, a fixture 100 may include a cartridge stimulating part 100f to stimulate the cartridge main body 200 (with reference to FIGS. 4, 9 and 10) inserted into the fixture 100 so as to cause release of a drug from the cartridge main body 220. Further, the cartridge pressing part 100e in accordance with the above-described embodiment causes drug release and may thus be one example of the cartridge stimulating part 100f.

In this embodiment, the cartridge stimulating part 100f may protrude from the inner surface of a cartridge hole 100 so as to penetrate the cartridge main body 220 to release the drug from the cartridge main body 220.

Penetration of the cartridge stimulating part 100f into the cartridge main body 220 means that the cartridge stimulating part 100f damages the membrane structure of the cartridge main body 220 and thus forms a path (a drug release path) through which the drug may be released. The cartridge main body 220 applied to the fixture 100 in accordance with this embodiment may have a single-layered membrane structure.

As apparent from the above description, a drug delivery implant implanted into a bone, i.e., a drug injection implant, in accordance with the present invention has effects, as follows.

First, the drug delivery implant in accordance with the present invention may continuously administer a drug into bone tissues of a designated region and mount a drug cartridge (a drug reservoir, a drug receptor or a drug carrier) together with a cap in a fixture under the condition that the drug cartridge is coupled with the cap so as to facilitate mounting of the drug cartridge in the fixture and replacement of the drug cartridge.

Second, the drug delivery implant in accordance with the present invention may prevent drug release before the drug cartridge is inserted into the fixture and then initiate drug release after the drug cartridge is mounted in the fixture, thereby performing stable drug administration at an implanted position, preventing drug leakage and adjusting the release amount of a drug.

Third, the drug delivery implant in accordance with the present invention may maintain an implanted state by coupling the upper part and the lower end part of the fixture, provided with screw threads formed on the outer circumferential surface thereof, with bone tissues, thereby minimizing damage to the bone tissues due to the screw threads, being easily removed after completion of drug administration, minimizing clogging of drug channels by bone dust, and facilitating manufacture of the fixture.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A drug delivery implant configured to be implanted into a bone, comprising:
   a hollow implant fixture provided with an inlet formed at an upper end thereof; and
   a drug supply cartridge coupled to the hollow implant fixture,
   wherein the drug supply cartridge includes:
      a cap for closing the inlet of the hollow implant fixture; and
      a cartridge main body provided under the cap, coupled with the cap so as to be mounted in the hollow implant fixture integrally with the cap, and accommodated in the hollow implant fixture to release a drug,
   wherein a cartridge hole to accommodate the cartridge main body and drug channels to guide a drug released from the inside of the cartridge main body to the outside of the hollow implant fixture are formed in the hollow implant fixture,
   wherein the cartridge main body includes:
      an outer membrane including first release holes to release the drug to the outside of the cartridge main body and forming an outer cover of the cartridge main body; and
      an inner membrane including second release holes closed by the outer membrane, stacked in the outer membrane and closing the first release holes, the first release holes and the second release holes being selectively communicable with each other by an external force applied to the cartridge main body.

2. The drug delivery implant according to claim 1, wherein the cap is detachably coupled to the upper end of the hollow implant fixture.

3. The drug delivery implant according to claim 2, wherein a female screw is formed on any one of the cap and the hollow implant fixture and a male screw for screw connection with the female screw is formed on the other of the cap and the hollow implant fixture.

4. The drug delivery implant according to claim 1, wherein the hollow implant fixture includes:
   an upper fixing part forming the upper end of the hollow implant fixture, provided with a first male screw formed on an outer circumferential surface thereof for being adapted to be fixed to a bone;
   a lower fixing part forming a lower end portion of the hollow implant fixture and provided with a second male screw formed on the outer circumferential surface thereof for being adapted to be fixed to the bone; and
   a screwless drug release part having a hollow shape connecting the upper fixing part and the lower fixing part and provided with the drug channels.

5. The drug delivery implant according to claim 4, wherein the second male screw of the lower fixing part is a tapping screw.

6. The drug delivery implant according to claim 4, wherein the lower fixing part includes the drug channels to guide the drug from the inside of the cartridge hole to the outside of the lower fixing part.

7. The drug delivery implant according to claim 1, wherein the cartridge hole includes a cartridge pressing part to pressurize the cartridge main body inserted into the hollow implant fixture so as to cause release of the drug from the cartridge main body.

8. The drug delivery implant according to claim 7, wherein the cartridge pressing part pressurizes the outer membrane of the cartridge main body and thus forms drug release paths in the cartridge main body so that the drug is released through the first release holes and the second release holes.

9. The drug delivery implant according to claim 8, wherein the cartridge pressing part protrudes upwards from the bottom of the cartridge hole.

10. The drug delivery implant according to claim 1, wherein the hollow implant fixture includes a cartridge stimulating part to stimulate the cartridge main body inserted into the hollow implant fixture so as to cause release of the drug from the cartridge main body.

11. The drug delivery implant according to claim 10, wherein the cartridge stimulating part protrudes from an inner surface of the cartridge hole so as to penetrate the cartridge main body to release the drug from the cartridge main body.

12. The drug delivery implant according to claim 1, wherein a tool groove for connection with a tool to rotate the hollow implant fixture is formed at the upper end of the hollow implant fixture.

13. The drug delivery implant according to claim 1, wherein a drug inlet is provided at an upper end of the cartridge main body and the upper end of the cartridge main body is sealed by the cap.

* * * * *